US009429664B2

(12) United States Patent
Crocco et al.

(10) Patent No.: US 9,429,664 B2
(45) Date of Patent: Aug. 30, 2016

(54) X-RAY DETECTOR AND X-RAY PHOTOGRAPHING APPARATUS INCLUDING THE SAME

(71) Applicant: SAMSUNG ELECTRONICS CO., LTD., Suwon-si (KR)

(72) Inventors: Jerome Crocco, Braga (PT); Ji-hoon Kang, Hwaseong-si (KR); Sung-kyu Park, Uiwang-si (KR); Jin-hwan Oh, Suwon-si (KR); Sang-min Lee, Suwon-si (KR); Min-kook Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 191 days.

(21) Appl. No.: 14/462,928

(22) Filed: Aug. 19, 2014

(65) Prior Publication Data

US 2015/0092918 A1    Apr. 2, 2015

(30) Foreign Application Priority Data

Sep. 27, 2013    (KR) .................. 10-2013-0115701

(51) Int. Cl.
| | |
|---|---|
| *G01T 1/24* | (2006.01) |
| *H01L 27/146* | (2006.01) |
| *H01L 31/08* | (2006.01) |
| *G01N 23/04* | (2006.01) |
| *G01T 7/00* | (2006.01) |

(52) U.S. Cl.
CPC .................. *G01T 1/24* (2013.01); *G01N 23/04* (2013.01); *G01T 7/00* (2013.01); *H01L 27/14676* (2013.01); *H01L 27/14696* (2013.01); *H01L 31/085* (2013.01)

(58) Field of Classification Search
CPC ..... G01T 1/24; G01T 1/2018; G01T 1/2928; G01T 1/241; G01T 1/208; G01T 1/00
See application file for complete search history.

(56) References Cited

U.S. PATENT DOCUMENTS

| | | | |
|---|---|---|---|
| 7,312,458 B2* | 12/2007 | Blevis ..................... | G01T 1/244 250/370.09 |
| 7,402,815 B2 | 7/2008 | Gagnon et al. | |

(Continued)

FOREIGN PATENT DOCUMENTS

| | | |
|---|---|---|
| JP | 2007-000626 A | 1/2007 |
| KR | 10-2000-0040228 A | 7/2000 |

OTHER PUBLICATIONS

Communication issued Sep. 25, 2015, issued by the Korean Intellectual Property Office in counterpart Korean Patent Application No. 10-2013-0115701.

(Continued)

*Primary Examiner* — Hoon Song
(74) *Attorney, Agent, or Firm* — Sughrue Mion, PLLC

(57) ABSTRACT

An X-ray detector and an X-ray imaging apparatus including the X-ray detector are provided. The X-ray detector includes a detector element including a cathode electrode and an anode electrode which are spaced apart from each other and a photoconductive layer located between the cathode electrode and the anode electrode and configured to absorb X-rays and generate electric charges, a first temperature controller configured to contact a first surface of the detector element and is configured to control a temperature of the cathode electrode, and a second temperature controller configured to contact a second surface of the detector element opposite to the first surface of the detector element and configured to control a temperature of the anode electrode.

20 Claims, 9 Drawing Sheets

(56) References Cited

U.S. PATENT DOCUMENTS

| | | |
|---|---|---|
| 7,514,692 B2 | 4/2009 | Bouhnik et al. |
| 7,652,258 B2 | 1/2010 | Shahar et al. |
| 8,135,109 B2 | 3/2012 | Hackenschmied et al. |
| 2007/0029496 A1 | 2/2007 | Bouhnik et al. |
| 2009/0065701 A1 | 3/2009 | Bale et al. |
| 2012/0193739 A1 | 8/2012 | Hackenschmied et al. |
| 2013/0108019 A1* | 5/2013 | Tkaczyk ................ A61B 6/037 378/62 |

OTHER PUBLICATIONS

Neimela et al., "High-Resolution p-i-n Cdte and CdZnTe X-Ray Detectors with Cooling and Rise-Time Discrimination", IEEE Transactions on Nuclear Science, Jun. 1996, 6 pages total, IEE Service Center, vol. 43, No. 3, New York, NY, USA.

Communication dated Nov. 13, 2014 issued by Korean Intellectual Property Office in counterpart Korean Patent Application No. 10-2013-0115701.

Communication date Jan. 23, 2015 issued by European Patent Office in counterpart European Patent Application No. 14184450.6.

* cited by examiner

X-RAY DETECTOR AND X-RAY PHOTOGRAPHING APPARATUS INCLUDING THE SAME

CROSS REFERENCE TO RELATED APPLICATION

This application claims priority from Korean Patent Application No. 10-2013-0115701, filed on Sep. 27, 2013, in the Korean Intellectual Property Office, the disclosure of which is incorporated herein in its entirety by reference.

BACKGROUND

1. Field

Apparatuses consistent with the exemplary embodiments relate to an X-ray detector, and an X-ray imaging apparatus including the same, and more particularly to an X-ray detector which reduces the occurrence of polarization, and an X-ray imaging apparatus including the same.

2. Description of the Related Art

X-ray detectors using thin-film transistors (TFTs) are receiving considerable attention as diagnostic X-ray detectors. X-ray detectors convert an X-ray image, obtained by performing an X-ray scan, or an X-ray projection image into a digital signal. The X-ray detectors are classified as direct mode detectors and indirect mode detectors.

A direct mode detector uses a photoconductor to convert X-rays directly into electric charges. An indirect mode detector uses a scintillator to convert X-rays into visible rays and then uses a photoelectric conversion device, such as a photodiode, to convert the visible rays into electric charges.

However, when X-rays are detected by using a direct mode detector, polarization may occur in a photoconductor layer, thereby hampering accurate detection of the X-rays.

SUMMARY

One or more exemplary embodiments include an X-ray detector configured to reduce the occurrence of polarization upon detection of X-rays and an X-ray imaging apparatus including the X-ray detector.

Additional aspects will be set forth in part in the description which follows and, in part, will be apparent from the description, or may be learned by practice of the presented exemplary embodiments.

According to one or more exemplary embodiments, an X-ray detector includes: a detector element including a cathode electrode and an anode electrode which are spaced apart from each other and a photoconductive layer located between the cathode electrode and the anode electrode, and configured to absorb X-rays and generate electric charges, a first temperature controller configured to contact a first surface of the detector element and configured to control a temperature of the cathode electrode, and a second temperature controller configured to contact a second surface of the detector element opposite to the first surface of the detector element and configured to control a temperature of the anode electrode.

At least one of the first and second temperature controllers may reduce an occurrence of polarization in the photoconductor layer by controlling the temperature of at least one of the cathode electrode and the anode electrode.

At least one of the first and second temperature controllers may control the temperature of at least one of the cathode electrode and the anode electrode so that a temperature difference between the cathode electrode and the anode electrode is greater than or equal to 30° C.

The first temperature controller may control the temperature of the cathode electrode to be greater than or equal to 50° C.

The second temperature controller may control the temperature of the anode electrode to be less than or equal to 20° C.

The first temperature controller may include a heating layer configured to heat the cathode electrode by applying a voltage to the cathode electrode.

The X-ray detector may further include a first insulating layer formed between the cathode electrode and the heating layer, a first electrode, and a second electrode separated from the first electrode by the heating layer.

The first electrode and the second electrode may be located on opposite sides of the heating layer so that the first electrode and the second electrode correspond to each other.

The first and second electrodes may be symmetrically located about a central axis of the X-ray detector.

The X-ray detector may further include a dummy electrode which does not overlap with the first electrode and the second electrode and is configured to be separate from the heating layer.

The X-ray detector may further include a second insulating layer formed between the dummy electrode and the heating layer.

The X-ray detector may further include a third electrode located on the heating layer, and the heating layer may heat the cathode electrode corresponding to a voltage that is applied between the cathode electrode and the third electrode.

The second temperature controller may include at least one of a thermoelectric element and a heat sink that will dissipate heat generated in the anode electrode.

When the second temperature controller includes a plurality of thermoelectric elements, the thermoelectric elements may be located separate from one another.

The detector element may further include a chip module substrate that is in contact with the anode electrode and generates an electrical signal corresponding to an electric charge generated in the photoconductive layer.

The second temperature controller may contact a bottom surface of the chip module substrate.

The second temperature controller may dissipate heat generated in the chip module substrate.

The chip module substrate may include a substrate having thermal conductivity.

The photoconductive layer may include cadmium zinc telluride (CdZnTe, or CZT).

According to one or more exemplary embodiments, an X-ray imaging apparatus includes an X-ray source for generating X-rays and an X-ray detector configured to detect X-rays transmitted by the X-ray source through an object, the X-ray detector including a detector element including a cathode electrode and an anode electrode which are spaced apart from each other and a photoconductive layer located between the cathode electrode and the anode electrode, and configured to absorb X-rays and generate electric charges, a first temperature controller configured to contact a first surface of the detector element and is configured to control a temperature of the cathode electrode, and a second temperature controller configured to contact a second surface of the detector element opposite to the first surface of the detector element and configured to control a temperature of the anode electrode.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
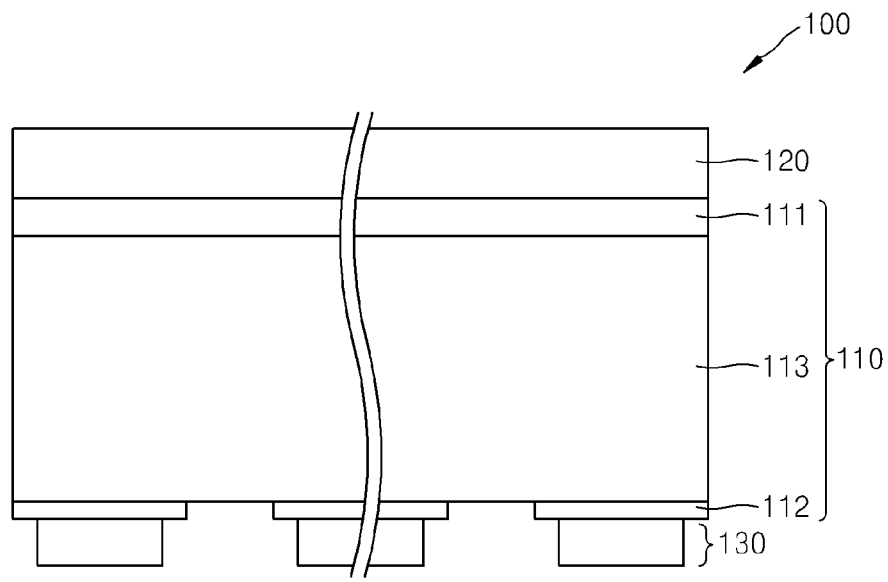
FIG. 1 is a schematic diagram of an X-ray detector according to an exemplary embodiment.

An X-ray detector and an X-ray imaging apparatus including the X-ray detector according to exemplary embodiments will now be described in detail with reference to the accompanying drawings. Since like reference numerals refer to like elements throughout, detailed descriptions thereof will be omitted here. Expressions such as "at least one of," when preceding a list of elements, modify the entire list of elements and do not modify the individual elements of the list.

In this specification, an "object" may be a human body or animal, or any portion of a human body or animal. For example, the object may be an internal organ, such as the liver, heart, uterus, brain, breast, and abdomen, or blood vessels. However, an object is not limited to these examples and an object could refer to any object that could be X-rayed. A "user" means a medical expert, and may be, but is not limited to, a doctor, a nurse, a medical technologist, a medical imaging expert, or a medical equipment repair technician.

Figure 2:
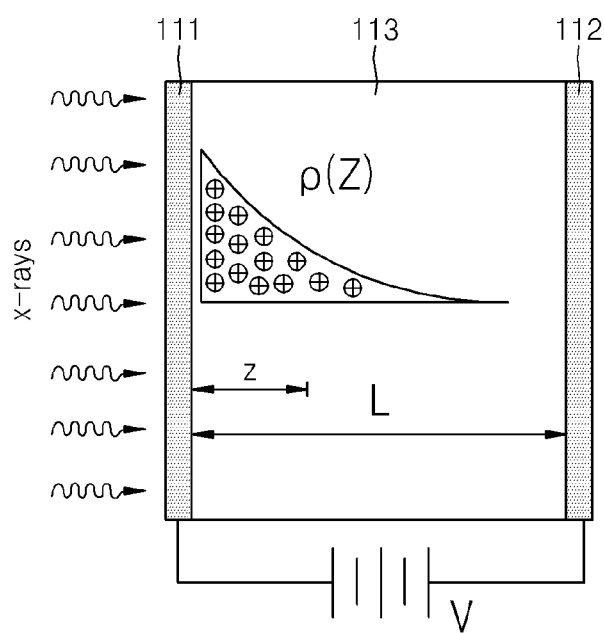
FIG. 2 is a reference diagram for explaining an occurrence of polarization in the X-ray detector of FIG. 1.

FIG. 1 is a schematic diagram of an X-ray detector 100 according to an exemplary embodiment, and FIG. 2 is a reference diagram for explaining an occurrence of polarization in the X-ray detector 100 of FIG. 1. Referring to FIGS. 1 and 2, the X-ray detector 100 according to the exemplary embodiment detects an X-ray that passes through an object and converts the X-ray into an electrical signal. The X-ray detector 100 includes a plurality of pixels that absorb X-rays and are arranged in a two-dimensional (2D) or one-dimensional (1D) array. Each pixel includes a cathode electrode 111, an anode electrode 112, and a photoconductive layer 113 located between the cathode electrode 111 and the anode electrode 112. The cathode electrode 111 and the anode electrode 112 are separate from each other. The photoconductive layer 113 absorbs X-rays and generates electric charges. The cathode electrode 111 and the photoconductive layer 113 are each formed as a single layer and may be common to all the pixels. A conductive layer is patterned into a plurality of anode electrodes 112. An anode electrode 112 is assigned to each pixel.

The cathode electrode 111 may be made of a transparent and electrically conductive material, such as indium tin oxide (ITO), through which X-rays can penetrate. The cathode electrode 111 is formed as a single layer so as to apply a common voltage to all of the pixels in the X-ray detector 100. An electric field may be created in the photoconductive layer 113 upon application of a voltage to the cathode electrode 111.

The photoconductive layer 113 may be formed of various materials such as amorphous selenium (a-Se), cadmium telluride (CdTe), cadmium zinc telluride (CdZnTe or CZT), mercuric iodide ($HgI_2$), lead iodide ($PbI_2$), lead oxide (PbO), and bismuth iodide ($BiI_3$). Upon absorption of the X-rays, the photoconductive layer 113 generates electric charges which cause an electrical signal to flow in the photoconductive layer 113.

The photoconductive layer 113 absorbs X-rays to generate electric charges, e.g., electron-hole pairs. In this case, electrons and holes in the electric charges move toward electrodes of opposite polarities. For example, holes and electrons may move toward the cathode electrode 111 and the anode electrode 112, respectively. While a velocity of the holes is lower than a velocity of the electrons, electrons are accelerated toward the anode electrode 112. Thus, as illustrated in FIG. 2, electrons reach the anode electrode 112 before the holes reach the cathode electrode 111, thereby causing polarization in the photoconductive layer 113.

As the amount of X-rays increase, polarization may occur at a greater extent. Electric charge density $\rho(Z)$ may increase according to the generation of space charges and the result of polarization, as defined by Equation (1) below:

$$\rho(Z) = q \frac{\Phi_\gamma \bar{E}_\gamma}{\varepsilon v_{eff}} e^{-Z/\Lambda} \quad \text{(Equation 1)}$$

where q is an electric charge within the photoconductive layer 113, $\Phi_\gamma$ is the amount of X-rays that enter the photoconductive layer 113, $\bar{E}_\gamma$ is a mean energy of incident photons of X-rays, $\Lambda$ is a distance by which the incident photon moves within the photoconductive layer 113 in a vertical (electrode) direction, c is an electron-hole pair creation energy, $v_{eff}$ is an effective velocity of an electric charge in the electric field, and Z is a distance between an electric charge that generates polarization and the cathode electrode 111.

As shown in Equation (1), polarization is closely related to the effective velocity $v_{eff}$ of the electric charges. The effective velocity $v_{eff}$ of electric charges is inversely proportional to a hole detrapping coefficient as defined by Equation (2) below, and the hole detrapping coefficient is inversely proportional to a temperature of the photoconductive layer 113 as defined by Equation (3) below;

$$v_{eff} = \frac{\mu_h \tau_h}{\tau_h + \tau_D} \frac{V}{L} \quad \text{(Equation 2)}$$

where $\tau_h$ and $\mu_h$ denote a hole detrapping coefficient and a hole mobility, respectively, V is a voltage applied between the cathode electrode 111 and the anode electrode 112, and L is a distance between the cathode electrode 111 and the anode electrode 112.

$$\tau_D = \frac{1}{v} \exp\left(\frac{E_A}{kT}\right) \quad \text{(Equation 3)}$$

where $E_A$, T, and k denotes a hole energy level, a temperature of the photoconductive layer 113, and Boltzmann constant, respectively. Thus, reducing polarization may be achieved by increasing the temperature of the photoconductive layer 113.

Increasing the temperature of the photoconductive layer 113 may be achieved by increasing the temperature of the cathode electrode 111. To increase the temperature of the cathode electrode 111, a first temperature controller 120 may include a heating layer 211 for heating the cathode electrode 111. The heating layer 211 may be formed of a material that generates heat when a voltage is applied to the heating layer 211. For example, the heating layer 211 may be made of carbon. Electrodes for applying a voltage to the heating layer 211 may be arranged in various configurations.

FIGS. 3 through 7 illustrate first temperature controllers 120a, 120b, 120c, 120d, and 240, respectively, according to various exemplary embodiments.

Figure 3:
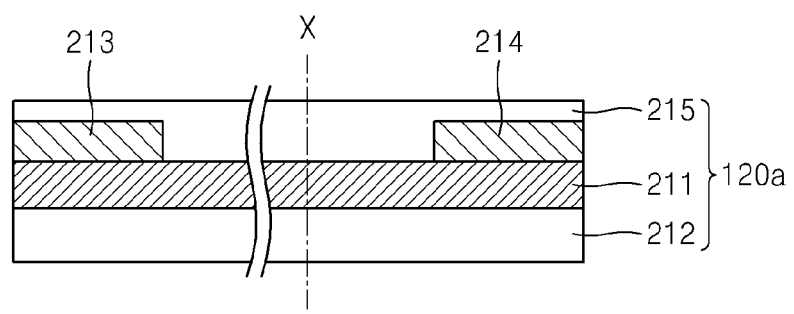
FIGS. 3 through 7 illustrate first temperature controllers according to various exemplary embodiments.

Referring to FIG. 3, the first temperature controller 120a includes a heating layer 211, a first insulating layer 212 located between the cathode electrode 111(shown in FIG. 1) and the heating layer 211, and a first electrode 213 and a second electrode 214 which are separated from each other on the heating layer 211. The first electrode 213 and the second electrode 214 may each be formed of a material having high X-ray permeability and electrical conductivity, such as silver (Ag). The first insulating layer 212 may be formed of an electrically insulating material that X-rays are able to penetrate.

The first electrode 213 and the second electrode 214 are located on either edge of the heating layer 211 so that they correspond to each other. For example, the first electrode 213 and the second electrode 214 are symmetrically located about a central axis X of the X-ray detector 100 (shown in FIG. 1). The first temperature controller 120a may further include a second insulating layer 215 that covers the first electrode 213 and the second electrode 214. The first insulating layer 212 and the second insulating layer 215 may each be formed of an insulating material with high X-ray permeability, such as polyethylene terephthalate (PET).

Figure 4:
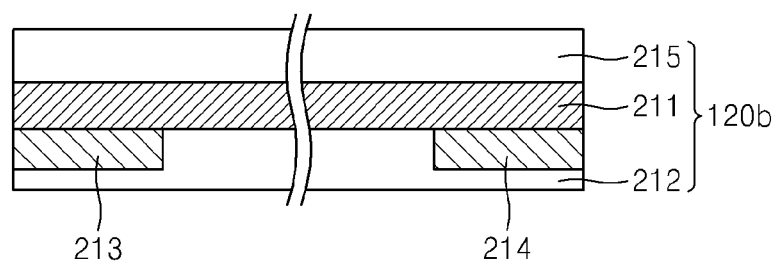

Although the first electrode 213 and the second electrode 214 are located on a top surface of the heating layer 211, they are not limited thereto. As illustrated in FIG. 4, the first electrode 213 and the second electrode 214 may be located on a bottom surface of the heating layer 211. When the first electrode 213 and the second electrode 214 are located on the bottom surface of the heating layer 211, the second insulating layer 215 may be omitted.

Due to such an arrangement of the first electrode 213 and the second electrode 214, the amount of X-rays that penetrate a region where the first electrode 213 and the second electrode 214 are located may be different from the amount of X-rays that penetrate a region where the first electrode 213 and the second electrode 214 are not located. Such a difference in the amount of X-rays may cause distortion of the resulting image. To prevent the risk of image distortion, referring to FIG. 5, a first temperature controller 120c may further include a dummy electrode 216 that does not overlap with the first electrode 213 and the second electrode 214 and is separated from the heating layer 211. The dummy electrode 216 may be formed of the same material as that of the first electrode 213 and the second electrode 214, but does not apply a voltage to the heating layer 211. The dummy electrode 216 compensates for a difference in the amount of X-rays due to the arrangement of the first electrode 213 and the second electrode 214.

Figure 5:
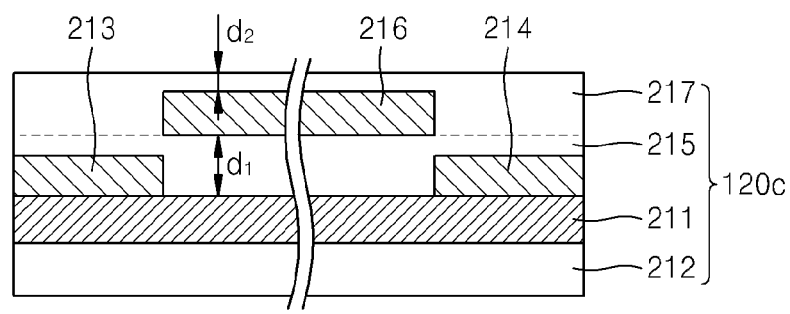

As illustrated in FIG. 5, the dummy electrode 216 may be located on the second insulating layer 215. The first temperature controller 120c may further include a third insulating layer 217 formed on the dummy electrode 216. A sum of thicknesses d1 and d2 of the second insulating layer 215 and the third insulating layer 217 may be uniform across the entire second insulating layer 215 and the third insulating layer 217.

Figure 6:
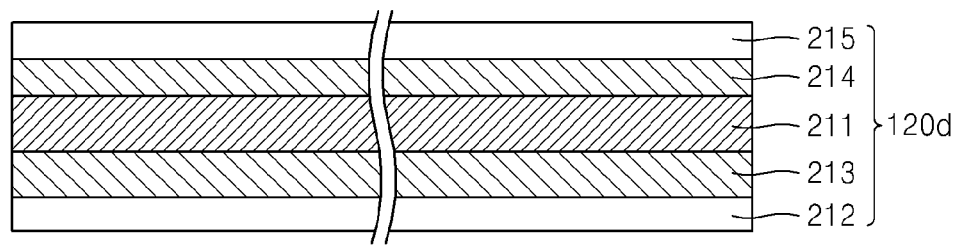

In another exemplary embodiment, referring to FIG. 6, a first temperature controller 120d may include a first insulating layer 212 on the cathode electrode 111, a first electrode 213 on the first insulating layer 212, a heating layer 211 on the first electrode 213, and a second electrode 214 on the heating layer 211. When necessary, a second insulating layer 215 may be located on the second electrode 214.

Figure 7:
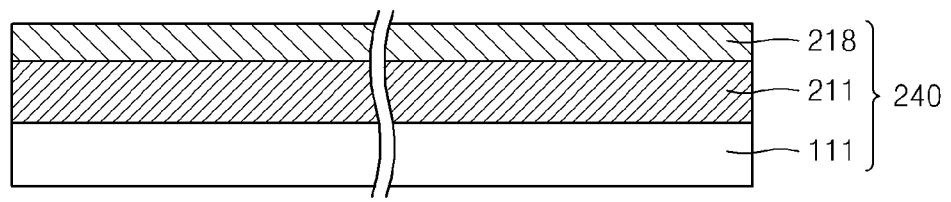

Furthermore, a voltage may be generated in the heating layer 211 through the cathode electrode 111. Referring to FIG. 7, the first temperature controller 240 includes a heating layer 211 and a third electrode 218 on the cathode electrode 111. The heating layer 211 may be located on the cathode electrode 111, and a third electrode 218 may be located on a top surface of the heating layer 211. The third electrode 218 may be located on the entire top surface of the heating layer 211, but is not limited thereto. For example, the third electrode 218 may be formed on a portion of the top surface of the heating layer 211. A voltage may also be applied between the third electrode 218 and the cathode electrode 111 to generate heat in the heating layer 211.

The first temperature controller 120 described above may control the temperature of the cathode electrode 111 so that a temperature difference between the cathode electrode 111 and the anode electrode 112 is greater than or equal to 30° C. In detail, the heating layer 211 is heated by a voltage applied by the first electrode 213 and the second electrode 214, and heat generated in the heating layer 211 is then transferred to the cathode electrode 111 so that a temperature difference between the cathode electrode 111 and the anode electrode 112 is greater than or equal to 30° C. Alternatively, the first temperature controller 120 may control the temperature of the cathode electrode 111 to be greater than or equal to 50° C.

Figure 8:
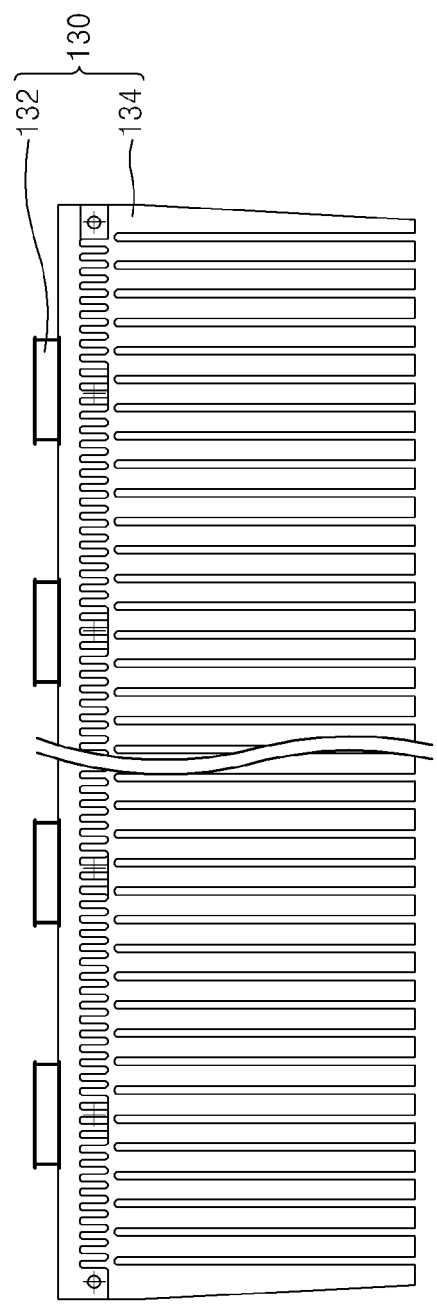
FIG. 8 illustrates a second temperature controller according to an exemplary embodiment.

In order to prevent the occurrence of polarization in the photoconductive layer 113, the temperature of the anode electrode 112 may be lowered. To decrease the temperature of the anode electrode 112, the X-ray detector 100 may further include a second temperature controller 130 that contacts a bottom surface of a detector element 110 proximate to the anode electrode 112 and controls the temperature of the anode electrode 112. As illustrated in FIG. 8, the second temperature controller 130 may include at least one of an active device, such as a thermoelectric element 132, and a passive device, such as a heat sink 134.

FIG. 8 illustrates the second temperature controller 130 in the X-ray detector 100 of FIG. 1. Referring to FIG. 8, a plurality of thermoelectric elements 132 are separated from one another and contact a portion of the detector element 110. The plurality of thermoelectric elements 132 may be arranged for each pixel, but are not limited thereto. For example, the plurality of thermoelectric elements 132 may be arranged for each group of pixels. The second temperature controller 130 may further include the heat sink 134 that connects the plurality of thermoelectric elements 132 to one another and transfers heat released by the plurality of thermoelectric elements 132 externally. The heat sink 134 may be a pin type so that its external surface area is maximized. While the second temperature controller 130 includes the plurality of thermoelectric elements 132 and the heat sink 134, the exemplary embodiments are not limited thereto. That is, the second temperature controller 130 may include only the plurality of thermoelectric elements 132 or a single heat sink 134. In another embodiment, the thermoelectric elements 132 may be integrated with the heat sink 134.

The second temperature controller 130 may control the temperature of the anode electrode 112 so that a temperature difference between the cathode electrode 111 and the anode electrode 112 is greater than or equal to 30° C. For example, the second temperature controller 130 may control the temperature of the anode electrode 112 to be less than or equal to 20° C. The second temperature controller 130 may improve electric charge mobility in the photoconductive layer 113 adjacent to the anode electrode 112 and provides high inter-pixel resistance to the anode electrode 112. Thus, the second temperature controller 130 may reduce a polarization phenomenon within the photoconductive layer 113.

Figure 9:
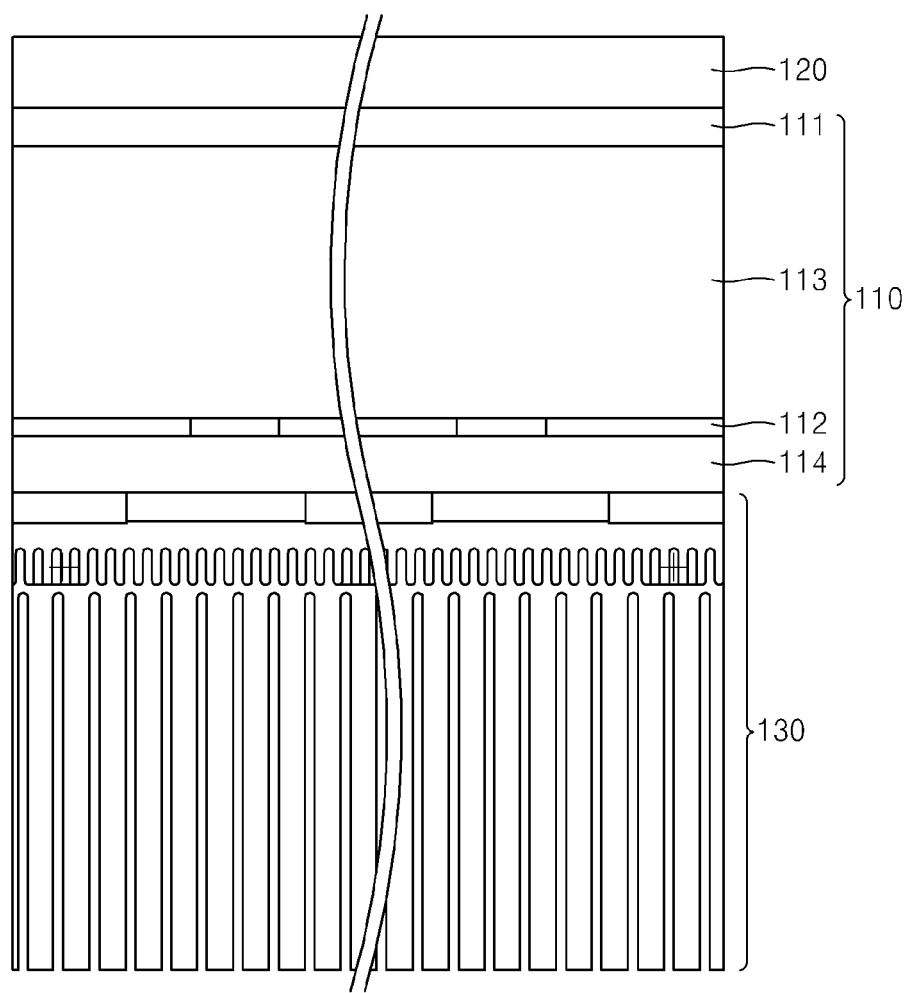
FIG. 9 illustrates an X-ray detector according to another exemplary embodiment.

FIG. 9 illustrates an X-ray detector according to another exemplary embodiment. Referring to FIG. 9, a detector element 110 includes a cathode electrode 111, a photoconductive layer 113, an anode electrode 112, and a chip module substrate 114 that is in contact with the anode electrode 112 and generates an electrical signal corresponding to an electric charge generated in the photoconductive layer 113. The chip module substrate 114 includes a read-out circuit, such as a thin film transistor (TFT) array (not shown), formed on a substrate. The TFT array may have a Metal Oxide Semiconductor Field Effect Transistor (MOSFET) structure in which an active layer is formed of amorphous silicon. The substrate may be formed of a material with thermal conductivity, such as metal or silicon.

One electrode (e.g., a source electrode or drain electrode) of each TFT in the TFT array is electrically connected to the anode electrode 112. Thus, when the photoconductive layer 113 absorbs X-rays to generate electric charges, holes of the electric charges move toward the cathode electrode 111 while electrons move toward the anode electrode 112, e.g., the one electrode such as a source or drain electrode of each TFT. Thus, the TFT array may read out an electrical signal corresponding to an electric charge generated by the photoconductive layer 113 at each pixel.

The second temperature controller 130 may be in contact with the anode electrode 112, or may be disposed on a bottom surface of the chip module substrate 114 as illustrated in FIG. 9. Heat generated in the photoconductive layer 113 may be transferred to the chip module substrate 114 through the anode electrode 112. The second temperature controller 130 may cool down the chip module substrate 114 to reduce noise due to heat from the chip module substrate 114.

Figure 10:
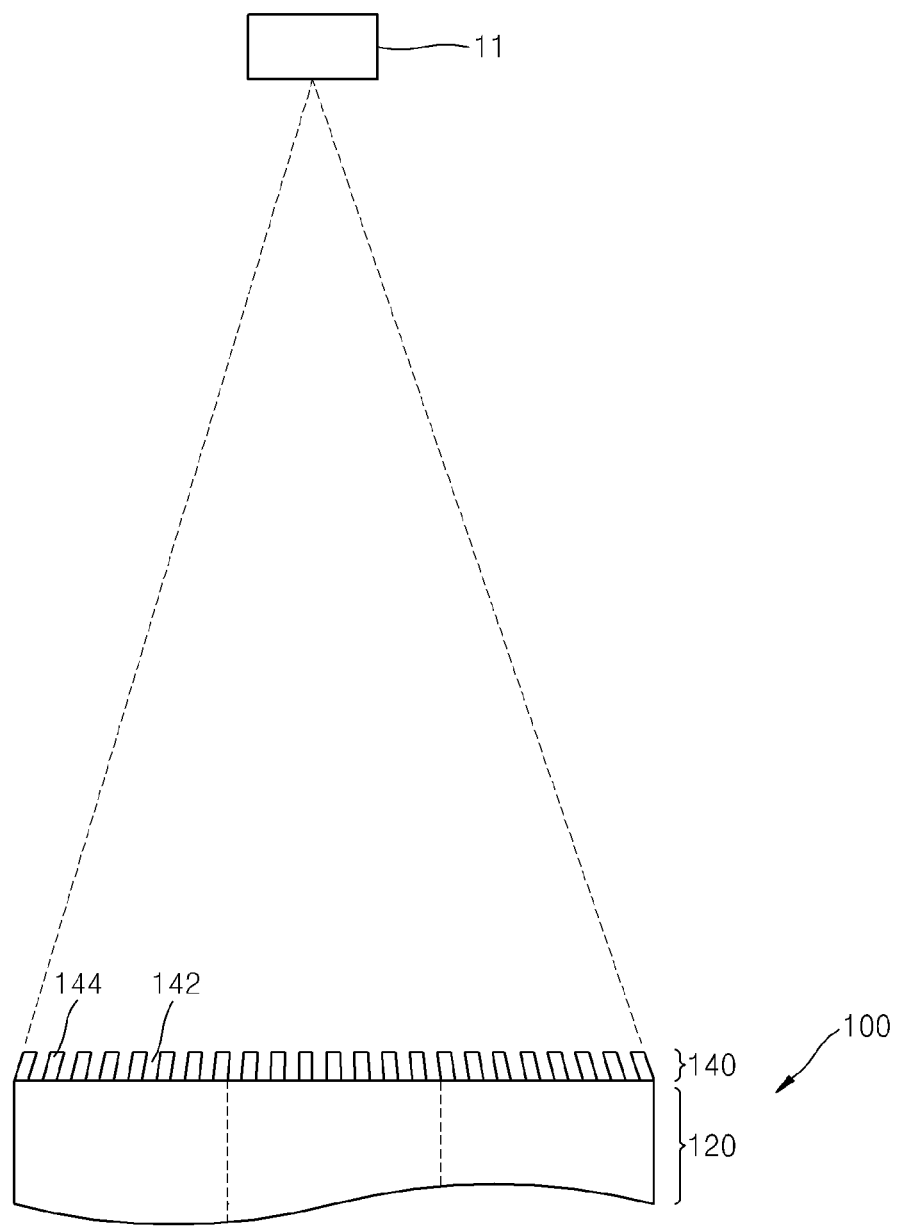
FIG. 10 illustrates an X-ray detector including an anti-scatter grid according to an exemplary embodiment.

When X-rays penetrate through an object or a medium, such as air, some of the X-rays may become scattered. In particular, when scattered X-rays are detected by the X-ray detector 100, the scattered X-rays cause noise in an image created by the X-rays. Thus, an X-ray detector according to an exemplary embodiment may further include an anti-scatter grid for removing scattered X-rays. FIG. 10 illustrates an X-ray detector 100 including an anti-scatter grid according to another exemplary embodiment including an anti-scatter grid 140.

Referring to FIG. 10, the anti-scatter grid 140 may be located on a first temperature controller 120. The anti-scatter grid 140 may have a structure similar to the patterns of X-rays so as to prevent the removal of non-scattered X-rays.

In detail, the anti-scatter grid 140 includes a plurality of X-ray paths 142 that allow X-rays to pass so that the X-rays are incident on the X-ray detector 100. The anti-scatter grid 140 also includes barrier walls 144 that define the plurality of X-ray paths in a 2D grid and blocks the propagation of X-rays between the X-ray paths 142.

The X-ray paths 142 may have a cross-section smaller than that of a pixel. In this case, the plurality of X-ray paths 142 may be arranged in a 2D array over an area occupied by one pixel. Furthermore, at least one of the X-ray paths 142 may be tapered so that its cross-section becomes wider in a direction from an X-ray source 11 toward the X-ray detector 100. X-rays are emitted from the X-ray source 11 and gradually diverge toward the X-ray detector 100. The X-ray paths 142 may be empty spaces, or may be filled with plastics that are permeable to X-rays. The barrier wall 144 may contain an X-ray absorbing material. Thus, X-rays impinging upon the barrier walls 144 are absorbed by the barrier walls 144. The barrier walls 144 may be formed of a material such as silver (Ag), gold (Au), tungsten (W), or molybdenum (Mo) which have a high atomic number.

As described above, each of the X-ray paths 142 have an empty space, or the X-ray path 142 may be filled with a material having good X-ray permeability, such as plastic, so as to increase the rigidity of the anti-scatter grid 140. In other words, even if the barrier walls 144 are thin, the material in the X-ray path 142 maintains the shape of the anti-scatter grid 140. Thus, the barrier walls 144 may be formed of a material with a low mechanical strength such as Au, Ag, or copper (Cu).

Furthermore, as described above, since the X-ray paths 142 have a small cross-section, the plurality of X-ray paths 142 may be arranged in a 2D array over an area corresponding to one pixel. Since a height of the barrier wall 142 is made proportional to a cross-section of the X-ray path 142 during manufacturing, the height of the barrier wall 142 may be decreased by reducing the cross-section of the X-ray path 142. This may also reduce the height of the anti-scatter grid 140, thereby achieving a compact design and efficient removal of scattered X-rays. Furthermore, alignment of the X-ray paths 142 on the area occupied by one pixel may enable removal of scattered X-rays in all directions.

The anti-scatter grid 140 having the above-described configuration may be located between an object and the X-ray detector 100 so that non-scattered X-rays are incident on the X-ray detector 100 and scattered X-rays are removed by the anti-scatter grid 140.

Figure 11:
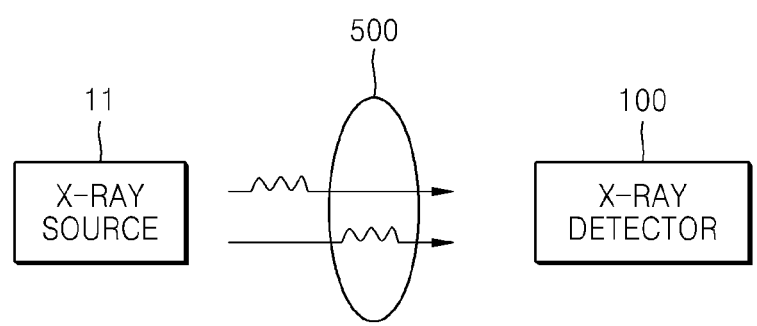
FIG. 11 is a block diagram of an X-ray imaging apparatus according to an exemplary embodiment.

The X-ray detector 100 and the X-ray source 11 are components of an X-ray imaging apparatus. FIG. 11 is a block diagram of an X-ray imaging apparatus according to an exemplary embodiment, and FIG. 12 illustrates an exterior appearance of a part of an X-ray imaging apparatus 10 according to an exemplary embodiment.

Figure 12:
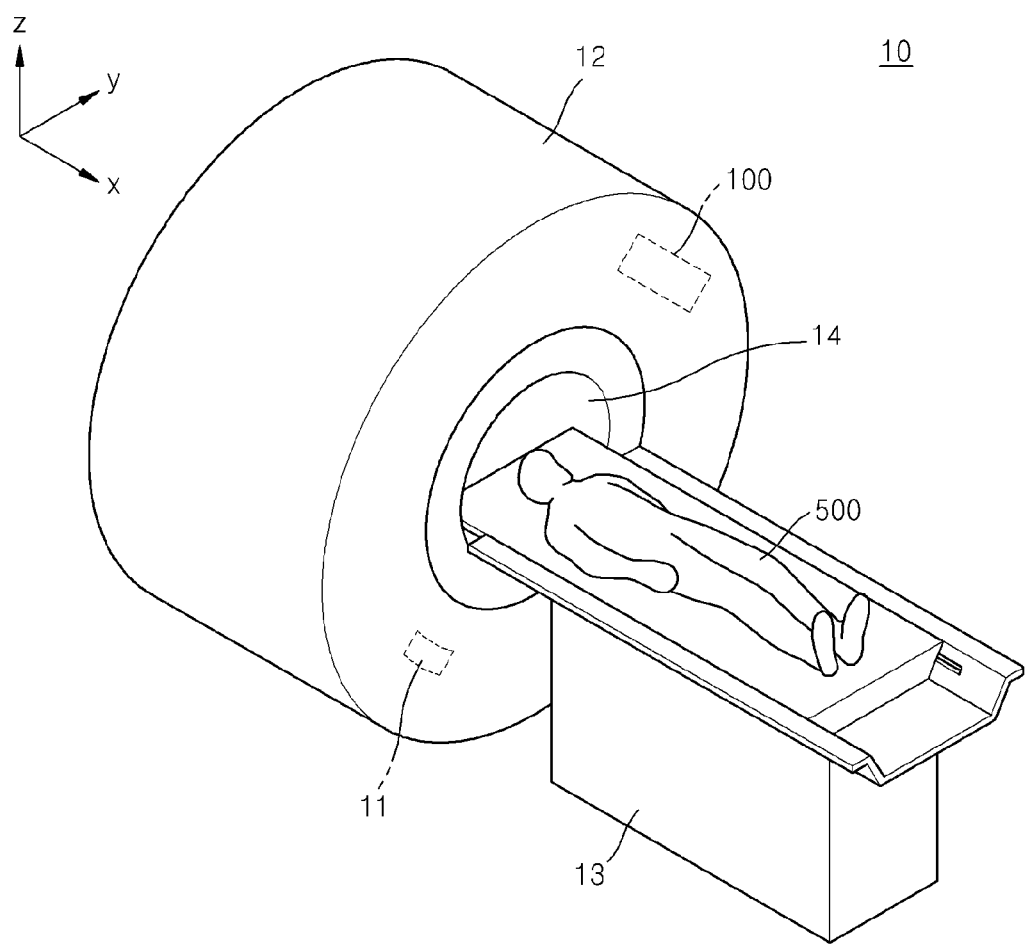
FIG. 12 illustrates an exterior appearance of part of an X-ray imaging apparatus according to an exemplary embodiment.

Referring to FIG. 11, the X-ray imaging apparatus may include an X-ray source 11 for emitting X-rays and an X-ray detector 100 for detecting X-rays that are transmitted through an object 500 (as shown in FIG. 12) among the emitted X-rays. The object may be, for example, a human body or body part but is not limited to these examples. The X-ray source 11 may include at least one X-ray generator (not shown) for generating X-rays. When the X-ray source 11 includes a plurality of X-ray generators, the X-ray generators may be arranged in a 1D or 2D array.

The plurality of X-ray generators may be independently driven to generate X-rays before transmitting them to the object 500, or some of the X-ray generators may be driven to generate X-rays before transmitting them to the object 500. Furthermore, at least one of the X-ray generators may be simultaneously or sequentially driven. Since the X-ray detector 100 described above with reference to FIGS. 1 through 10 is used as the X-ray detector 100 in FIGS. 11 and 12, a detailed description thereof will be omitted here.

Referring to FIG. 12, the X-ray imaging apparatus 10 according to the exemplary embodiment may further include a gantry 12 and an examination table 13. The gantry 12 has a cylindrical opening 14 at a central portion thereof, through which the object 500 is inserted. The inside of the gantry 12 may also include an X-ray source 11 for emitting X-rays and an X-ray detector 100 for detecting X-rays transmitted through the object 500. The X-ray source 11 is located opposite to the X-ray detector 100 so that the object 500 is located at a center of a predetermined region formed around the opening 14 of the gantry 12. For example, the X-ray source 11 and the X-ray detector 100 may be located inside the gantry 12 so as to vertically receive X-rays.

The gantry 12 is driven by a gantry driver (not shown) which rotates around the object 500 lying on the examination table 13 at a 360 degree angle or at a predetermined angle so that the object 500 may be imaged by the X-ray source 11 and the X-ray detector 100 from different angles. The gantry driver may move the gantry 12 back and forth along a horizontal direction, i.e., along the x-axis, so that a portion of the object 500 to be imaged may be located at the center of the interior of the gantry 12. The gantry driver may be located inside or outside of the gantry 12.

The examination table 13 consists of a bed having a predetermined area on which an object 500, such as a patient, lies still. The examination table 13 also includes an examination table driver (not shown) located at a predetermined portion of the examination table 13 for moving the examination table 13 toward the opening 14 located in the center of the gantry 12. The examination table 13 may be driven by the examination table driver to move back and forth horizontally so that a portion of the object 500 to be imaged is located at the center of the interior of the gantry 12. The examination table driver may move the examination table 13 up or down, i.e., along the z-axis, or left or right, i.e., along the y-axis, so as to acquire a clear image. Although the X-ray imaging apparatus 10 shown in FIG. 12 is a computed tomography (CT) apparatus, the exemplary embodiments are not limited thereto, and any other imaging apparatus using X-rays as a source may be used.

The X-ray imaging apparatus 10 may further include a signal processor for acquiring an image by using the result of the detection by the X-ray detector 100, a display unit for displaying the image, an input unit for receiving a user's command, and a control unit for controlling the overall operation of the X-ray imaging apparatus 10. However, since these components are well known in the art, detailed descriptions thereof will be omitted here.

As described above, X-ray detectors and X-ray imaging apparatuses according to one or more exemplary embodiments may reduce the occurrence of polarization.

While one or more exemplary embodiments have been described with reference to the figures, it will be understood by one of ordinary skill in the art that various changes in form and details may be made therein without departing from the spirit and scope of the inventive concept as defined by the following claims. Thus, it should be understood that the exemplary embodiments described herein should be considered in a descriptive sense only and not for purposes of limitation. All modifications and substitutions within the scope of the appended claims and their equivalents will be construed as being included in the exemplary embodiments.

What is claimed is:

1. An X-ray detector comprising:
    a detector element including a cathode electrode and an anode electrode which are spaced apart from each other and a photoconductive layer located between the cathode electrode and the anode electrode, and configured to absorb X-rays and generate electric charges;
    a first temperature controller configured to contact a first surface of the detector element and is configured to control a temperature of the cathode electrode; and
    a second temperature controller configured to contact a second surface of the detector element opposite to the first surface of the detector element and configured to control a temperature of the anode electrode.

2. The X-ray detector of claim 1, wherein at least one of the first temperature controller and the second temperature controller is configured to reduce an occurrence of polarization in the photoconductor layer by controlling the temperature of at least one of the cathode electrode and the anode electrode.

3. The X-ray detector of claim 1, wherein at least one of the first temperature controller and the second temperature controller is configured to control the temperature of at least one of the cathode electrode and the anode electrode so that a temperature difference between the cathode electrode and the anode electrode is greater than or equal to 30° C.

4. The X-ray detector of claim 1, wherein the first temperature controller is configured to control the temperature of the cathode electrode to be greater than or equal to 50° C.

5. The X-ray detector of claim 1, wherein the second temperature controller is configured to control the temperature of the anode electrode to be less than or equal to 20° C.

6. The X-ray detector of claim 1, wherein the first temperature controller includes a heating layer configured to heat the cathode electrode by applying a voltage to the cathode electrode.

7. The X-ray detector of claim 6, further comprising:
    a first insulating layer formed between the cathode electrode and the heating layer;
    a first electrode; and
    a second electrode separated from the first electrode by the heating layer.

8. The X-ray detector of claim 6, wherein the first electrode and the second electrode are located on opposite sides of the heating layer so that the first electrode and the second electrode correspond to each other.

9. The X-ray detector of claim 6, wherein the first electrode and the second electrode are symmetrically located about a central axis of the X-ray detector.

10. The X-ray detector of claim 6, further comprising a dummy electrode which does not overlap with the first electrode and the second electrode and is configured to be separate from the heating layer.

11. The X-ray detector of claim 6, further comprising a second insulating layer formed between the dummy electrode and the heating layer.

12. The X-ray detector of claim 6, further comprising a third electrode located on the heating layer,
    wherein the heating layer heats the cathode electrode corresponding to a voltage that is applied between the cathode electrode and the third electrode.

13. The X-ray detector of claim 1, wherein the second temperature controller comprises at least one of a thermoelectric element and a heat sink that dissipates heat generated in the anode electrode.

14. The X-ray detector of claim 13, wherein when the second temperature controller comprises a plurality of thermoelectric elements, and wherein the plurality of thermoelectric elements are located separate from each other.

15. The X-ray detector of claim 1, wherein the detector element further comprises a chip module substrate configured to contact the anode electrode and is configured to generate an electrical signal corresponding to an electric charge generated in the photoconductive layer.

16. The X-ray detector of claim 15, wherein the second temperature controller is configured to contact a bottom surface of the chip module substrate.

17. The X-ray detector of claim 16, wherein the second temperature controller is configured to dissipate heat generated in the chip module substrate.

18. The X-ray detector of claim 15, wherein the chip module substrate comprises a substrate having thermal conductivity.

19. The X-ray detector of claim 1, wherein the photoconductive layer comprises cadmium zinc telluride (CdZnTe, or CZT).

20. An X-ray imaging apparatus comprising:

an X-ray source configured to generate X-rays; and an X-ray detector configured to detect X-rays transmitted by the X-ray source through an object, the X-ray detector comprising:

a detector element including a cathode electrode and an anode electrode which are spaced apart from each other and a photoconductive layer located between the cathode electrode and the anode electrode, and configured to absorb X-rays and generate electric charges;

a first temperature controller configured to contact a first surface of the detector element and is configured to control a temperature of the cathode electrode; and a second temperature controller configured to contact a second surface of the detector element opposite to the first surface of the detector element and configured to control a temperature of the anode electrode.

* * * * *